United States Patent [19]

LeRette

[11] Patent Number: 4,905,508

[45] Date of Patent: Mar. 6, 1990

[54] RADIATOR HOSE HYDROMETER

[75] Inventor: David L. LeRette, Omaha, Nebr.

[73] Assignee: Thomas A. Ramona, Omaha, Nebr.

[21] Appl. No.: 309,351

[22] Filed: Mar. 9, 1989

[51] Int. Cl.⁴ .......................................... G01M 15/00
[52] U.S. Cl. ..................................... 73/118.1; 73/445
[58] Field of Search ...................... 73/118.1, 440, 323, 73/445; 123/198 D; 340/450

[56] References Cited

U.S. PATENT DOCUMENTS

| | | | |
|---|---|---|---|
| 1,578,193 | 3/1926 | Drake . | |
| 1,760,937 | 6/1930 | Dietrich | 73/440 X |
| 2,002,183 | 5/1935 | Lecarpentier | 265/46 |
| 2,212,809 | 8/1940 | Ericson | 265/46 |
| 3,054,391 | 9/1962 | Rocklen | 123/41.15 |
| 3,096,748 | 7/1963 | Harry | 123/41.15 |
| 3,292,427 | 12/1966 | Mattson | 73/118 |
| 3,908,467 | 9/1975 | Schwen et al. | 73/454 |
| 4,682,493 | 7/1987 | Tenenbaum | 73/118.1 |
| 4,736,628 | 4/1988 | Lin | 73/440 |

Primary Examiner—Jerry W. Myracle
Attorney, Agent, or Firm—Zarley, McKee, Thomte, Voorhees & Sease

[57] ABSTRACT

A radiator hose hydrometer includes a substantially horizontally disposed transparent tubular conduit interposed in the upper radiator hose of a liquid cooled engine. A hydrometer is mounted within the tubular conduit and is comprised of a series of arcuate transparent tubular members having apertures therethrough permitting the free flow of coolant into the tubular member. A float is operably secured within each tubular member, and is formed from a material which will float in liquid of a predetermined specific gravity. Each float is formed from materials having different specific gravities. Printed indicia on the conduit permits determination of the coolant's specific gravity and the coolant's level. Additionally, a radiator hose hydrometer having offset adapter permits use with upper radiator hoses having a diameter different than said conduit for leveling the device.

8 Claims, 3 Drawing Sheets 4,905,508

RADIATOR HOSE HYDROMETER

TECHNICAL FIELD

This invention generally relates to radiator hose hydrometers and more particularly to an improved hydrometer which permits safe, rapid and accurate analysis of specific gravity, level and condition of engine coolant.

BACKGROUND OF THE INVENTION

As is well-known, a liquid-cooled engine can be severely damaged if the cooling system fails to function properly. The effectiveness of the cooling system is largely determined by the amount of coolant in the system, as well as the amount of contamination of the liquid coolant and whether the coolant is circulating within the system. Typically, the coolant's level, color and clarity is visually inspected by removing the radiator cap and observing the coolant therein. While the coolant's level can be readily determined, the accuracy of such a visual inspection with regards to color and clarity is less than desirable. Further, the specific gravity of the coolant cannot be determined without the aid of a hydrometer. The inability to immediately determine the coolant's specific gravity by cursory inspection is a serious drawback, since the coolant's specific gravity determines the freezing point of the coolant.

Visual inspection of the coolant by removal of the radiator cap has other drawbacks as well. There is a risk of serious burns, which can occur if the radiator cap is removed from a hot engine. Secondly, this method does not encourage one to frequently inspect the coolant, since the radiator cap must be removed and a hydrometer purchased. Furthermore, this method does not permit the determination of whether the coolant is flowing or is blocked.

While there are several United States patents directed to devices interposed in radiator hoses to allow determination of the coolant level, they do not permit the user to determine the coolant's specific gravity. Furthermore, they are designed for a single, specific diameter radiator hose. Thus, manufacturers and distributors must stock a large inventory of various sizes and parts for consumers. Additionally, such devices will give inaccurate readings as to the coolant's level in those instances where the radiator hose and prior art device is inclined.

It is therefore a principal object of the present invention to provide a radiator hose hydrometer which permits rapid, safe and accurate analysis of the engine coolant.

Another object of the present invention is to provide a radiator hose hydrometer which permits easy and rapid determination of the radiator fluid's specific gravity.

A further object of the instant invention is to provide a radiator hose hydrometer which permits a visual determination as to the coolant's level, clarity, contamination and coolant flow.

Still another object of the invention is to provide a radiator hose hydrometer which allows visual inspection of the engine coolant's specific gravity, color, fluid level, clarity and coolant flow without having to remove the radiator cap.

An additional object of the present invention is to provide a radiator hose hydrometer which can be leveled within an inclined radiator hose.

Yet a further object is to provide a radiator hose hydrometer which may be utilized with radiator hoses having different diameters.

These and other objects of the present invention will be apparent to those skilled in the art.

SUMMARY OF THE INVENTION

The radiator hose hydrometer of this invention is mounted in a substantially horizontally disposed transparent tubular conduit interposed in the upper radiator hose of a liquid cooled engine. The transparent tubular conduit permits visual inspection of the coolant passing therethrough.

A hydrometer is mounted within the tubular conduit and is comprised of a series of arcuate transparent tubular members having apertures therethrough permitting the free flow of coolant into the tubular member. A float is operably secured within each tubular member, and is formed from a material which will float in liquid of a predetermined specific gravity. Each float is formed from material of various specific gravities, so that the specific gravity of the coolant can be determined by the specific float or floats which float in the coolant. Printed indicia on the conduit permits determination of the coolant's specific gravity. Additional printed indicia on the transparent tubular conduit permits determination of the coolant's level.

Offset adapters are secured to the ends of the tubular conduit permitting the tubular conduit to be interposed in an upper radiator having an inner diameter different than the tubular conduit. A second embodiment of the offset adapter permits the additional function of leveling the tubular conduit.

DESCRIPTION OF THE PREFERRED EMBODIMENT

Figure 1:
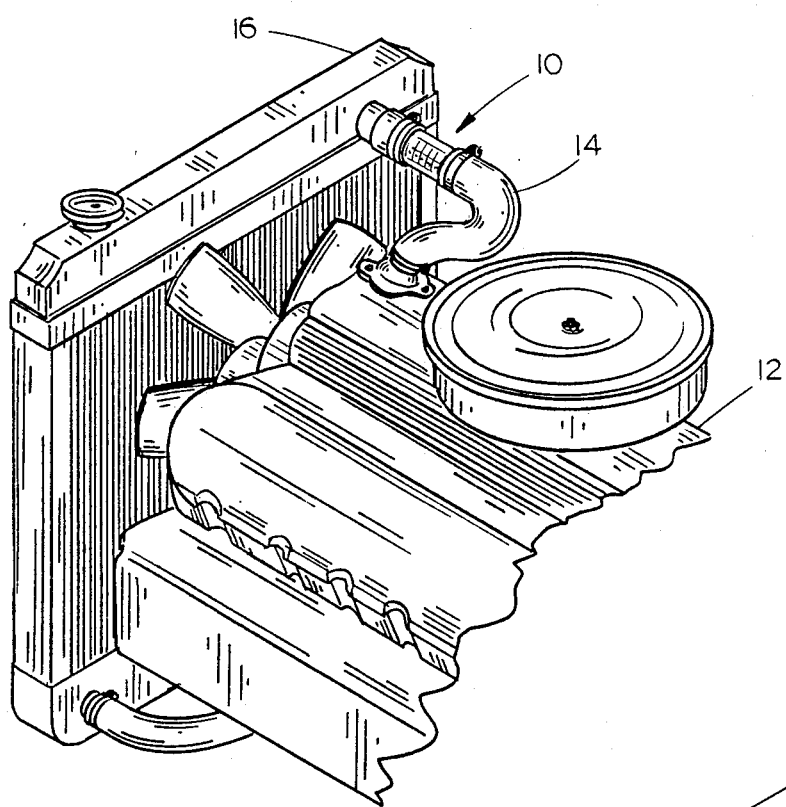
FIG. 1 is a perspective view of the present invention installed in the upper radiator hose of a liquid cooled internal combustion engine.

Referring now to the drawings, in which identical or corresponding parts are identified by the same reference numeral, the radiator hose hydrometer of this invention is designated generally at 10. As seen in FIG. 1, the radiator hose hydrometer 10 is interposed in an upper radiator hose 14 connecting a liquid cooled internal combustion engine 12 and a radiator 16. The radiator hose hydrometer 10 is located such that it is substantially horizontal.

Figure 2:
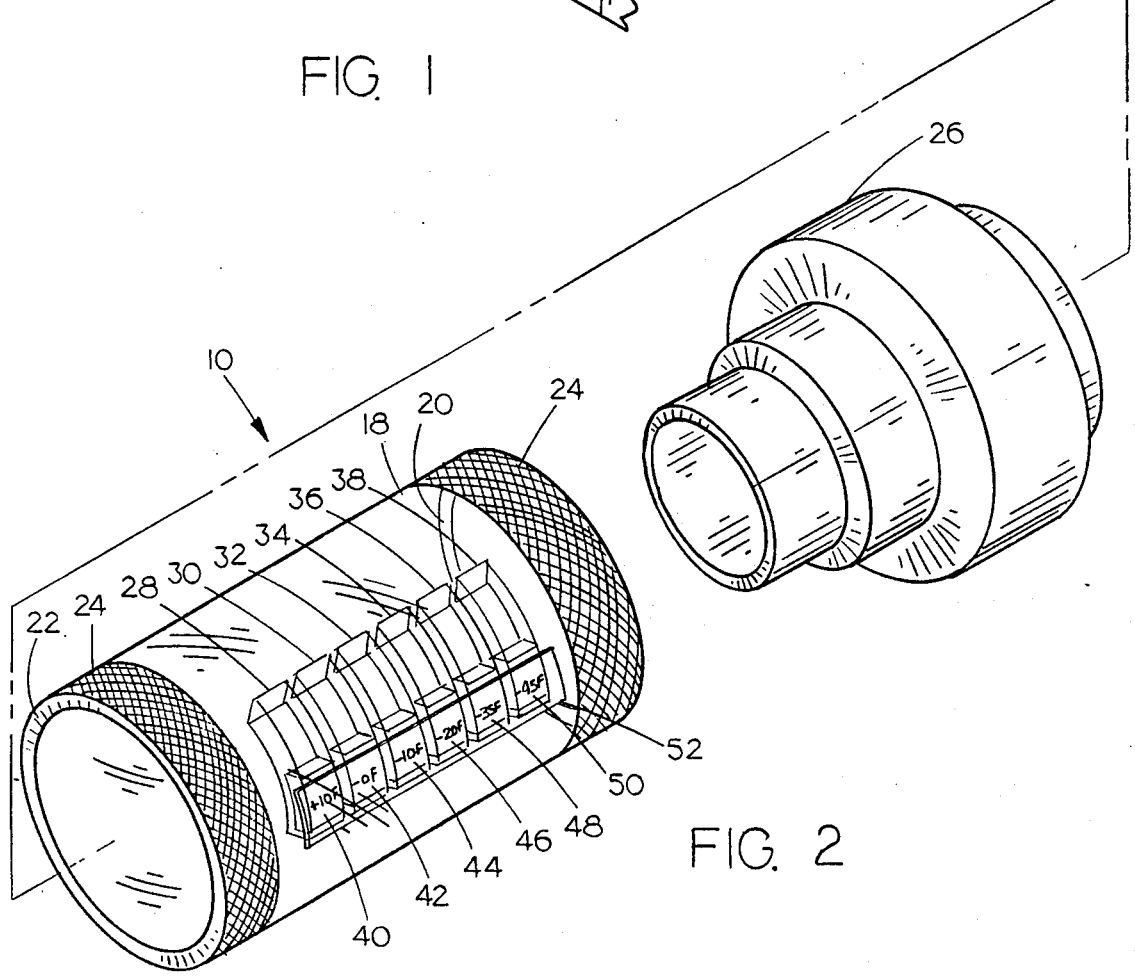
FIG. 2 is a perspective view of the invention having an offset adaptor removed from one end thereof.

As seen in FIG. 2, the radiator hose hydrometer 10 is comprised of a transparent tubular conduit 18 having a first end 20 and second end 22. A roughened area 24 is formed on the exterior of first end 20 and second end 22 and extends circumferentially around conduit 18 which grips the interior surface of the adjacent radiator hose to firmly mount conduit 18 in position.

An offset adaptor 26 is secured to conduit ends 20 and 22 permitting the radiator hose hydrometer lo to be utilized with various diameters of radiator hoses. Offset adapter 26 is utilized in those cases where conduit 18 is interposed in a substantially horizontal section of upper radiator hose 14.

A plurality of arcuate transparent tubular members 28, 30, 32, 34, 36 and 38 are mounted generally vertically along the interior wall of conduit 18 and have plastic floats 40, 42, 44, 46, 48 and 50 operably mounted therein, as indicated in FIG. 2. The plastic floats 40, 42, 44, 46, 48 and 50 are formed of a material which will float in liquid coolant of a predetermined specific gravity. Printed indicia 52 on a strip 53 on conduit 18 assists the user in determining the specific gravity of the floats, and thus, the specific gravity of the coolant.

Figure 3:
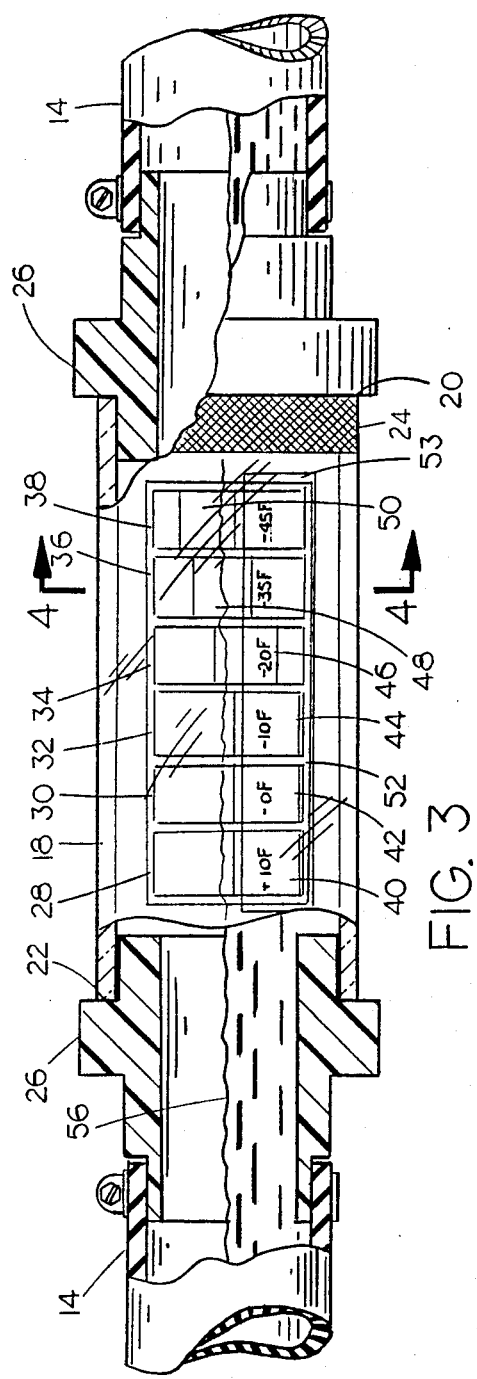
FIG. 3 is a side elevational view of the invention with portions in sectional view showing connection to the radiator hose.
Figure 4:
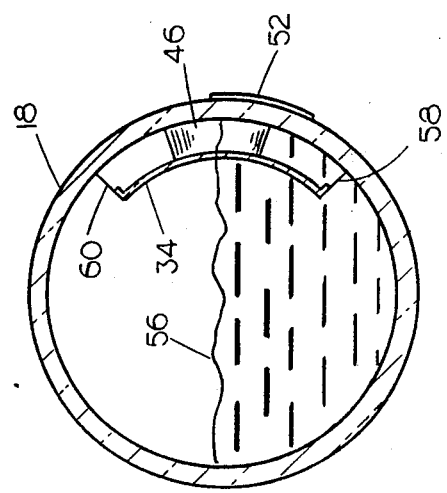
FIG. 4 is a cross-sectional view of the present invention.

As seen in FIG. 3, the radiator hose hydrometer has a liquid coolant 56 passing therethrough and floats, 40, 42, 44, 46, 48 and 50 indicate that this specific coolant is safe to a level of negative 10° F. This result is derived from observing the fact that floats 40, 42 and 44 are not floating, and are aligned with printed indicia 52 on strip 53 so as to enable a person to view the indicia. The transparent nature of conduit 18 permits the visual inspection of the color and clarity of coolant 56. Additionally, the flow of the coolant 56 passing therethrough can be readily observed -- which provides a rapid means for determining if the thermostat is stuck. Thus, the conduit 18 provides yet another safety factor. The location of strip 53 additionally permits the user to establish whether the coolant level within conduit 18 is of a sufficient level. As illustrated in FIG. 4, coolant 56 is at a level that is below the upper edge of the strip 53, thus indicating that the coolant level is not sufficient.

Figure 5:
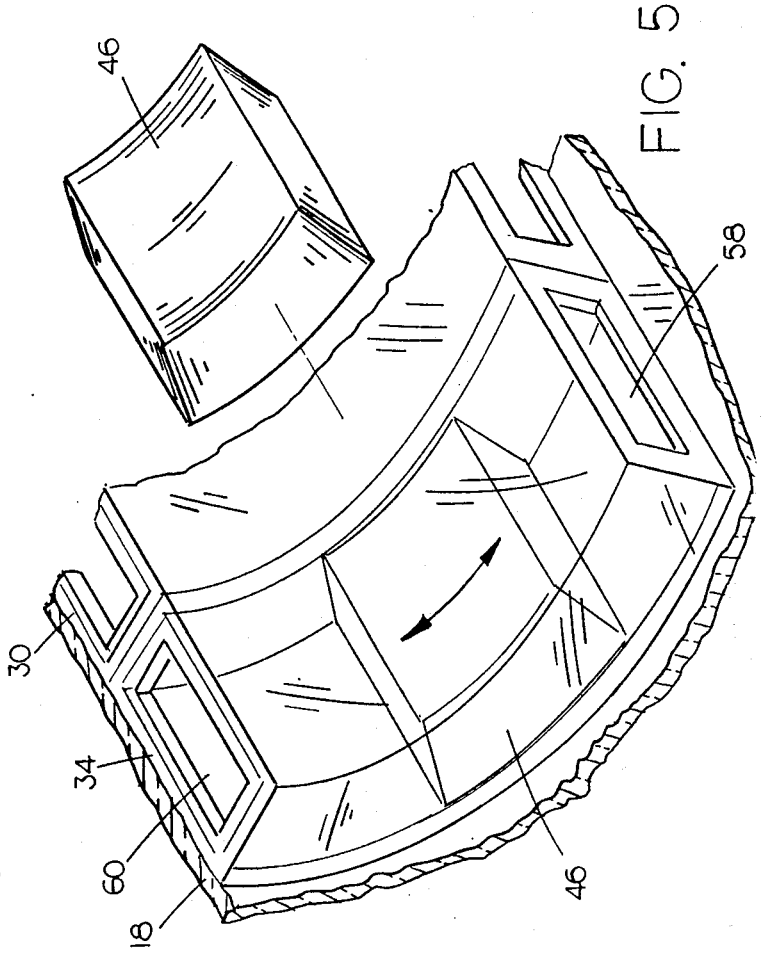
FIG. 5 is a perspective view of the hydrometer of the present invention.

Apertures 58 and 60 are formed in tubular member 34 to permit the free flow of liquid coolant therethrough. Each of the tubular members 28, 30, 32, 34, 36 and 38 have apertures therein which permit the free flow of coolant therein. Float 46, as illustrated in FIG. 5, is oriented in tubular member 34 to move vertically within the confines of the tubular member 34, in response to the specific gravity of coolant therein. The ends of tubular member 34 are constricted to restrain the float within the confines of the tubular member.

Figure 6:
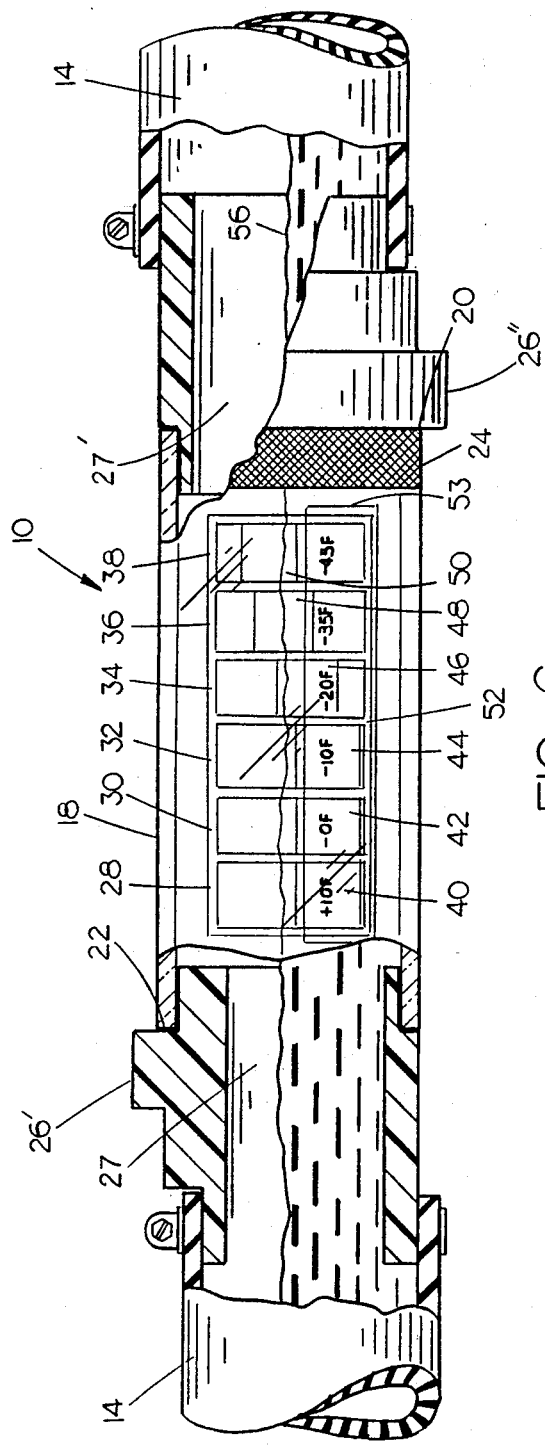
FIG. 6 is a perspective view of a hydrometer of the present invention having a second embodiment of an offset adapter secured to the ends thereof.

A second embodiment of the offset adapter is illustrated in FIG. 6, and is utilized in those instances where the upper radiator hose 14 has no substantially horizontal segment into which conduit 18 may be interposed. Offset adapter 26' is secured to the first end 20 and offset adapter 26'' is secured to second end 22. Offset adapter 26' has a bore 27 extending therethrough with longitudinal axis of bore 27 being offset from the longitudinal axis of conduit 18. Offset adapter 26'' has a bore 27 extending therethrough with longitudinal axis of bore 27' being offset from the longitudinal axis of conduit 18. Offset adapter 26' is secured to conduit 18 such that the longitudinal axis of bore 27 and longitudinal axis bore 27' are opposite of each other. Thus, by rotating conduit 18 about its longitudinal axis, first end 22 will move upwardly and second end 24 will move downwardly. Thus, conduit 18 can be leveled and the level of coolant 56 can accurately be determined.

It can thus be seen that the above mentioned invention accomplishes at least all of its stated objectives.

I claim:

1. In combination with a liquid cooled engine having an upper radiator hose extending therefrom to a radiator, a radiator hose hydrometer, comprising:

a substantially horizontally disposed transparent tubular conduit means interposed in said upper radiator hose and having first and second ends, said transparent tubular conduit permitting visual inspection of the color and level of the coolant passing through said radiator hose and said tubular conduit means, and means in said transparent tubular conduit means for indicating the specific gravity of the coolant passing therethrough and hence the approximate freezing point of the said coolant, including:

at least one transparent tubular member mounted completely within said conduit means and having an aperture therethrough permitting free flow of said coolant into said tubular member, and float means operably mounted within said tubular member and formed of a material which will float in coolant of a predetermined specific gravity, said float means mounted for movement between an upper floating position and a lower non-floating position.

2. The radiator hose hydrometer of claim 1 wherein said tubular conduit means further includes printed indicia thereon located with respect to said specific gravity indicating means to visually determine the sufficiency of the level of coolant within said conduit means, and thereby the sufficiency of the level of coolant within the engine.

3. The radiator hose hydrometer of claim 1 wherein said tubular conduit means further includes printed indicia thereon located with respect to said specific gravity indicating means to visually determine the specific gravity of the coolant.

4. The radiator hose hydrometer of claim 1 wherein the means for indicating the specific gravity of the coolant further includes a plurality of additional transparent tubular members mounted generally parallel to said at least one tubular member, completely within said conduit means, each said additional tubular member having apertures therethrough permitting free flow of said liquid coolant into said tubular member, and float means operably mounted within each said additional tubular member formed of a material which will float in coolant of a predetermined specific gravity, each of said tubular member having floats formed of different materials responsive to coolant of different predetermined specific gravities.

5. In combination with a liquid cooled engine having an upper radiator hose extending therefrom to a radiator, a radiator hose hydrometer, comprising:

a substantially horizontally disposed transparent tubular conduit means interposed in said upper radiator hose and having first and second ends, said transparent tubular conduit permitting visual inspection of the color and level of the coolant passing through said radiator hose and said tubular conduit means, and means in said transparent tubular conduit means for indicating the specific gravity of the coolant passing therethrough and hence the approximate freezing point of the said coolant, said radiator hose having a different diameter than said tubular conduit means, and offset adapter means secured to each of said first and second ends of the said conduit means to mount said conduit means in said radiator hose.

6. The radiator hose hydrometer of claim 5 further comprising a first offset adapter means secured to said first end of said conduit means, said first offset adapter means having a bore extending therethrough, said bore being offset with respect to the longitudinal axis of said conduit means, a second offset adapter means having a bore extending therethrough, said bore being offset with respect to the longitudinal axis of said conduit means and said bore of said first offset adapter means and thereby permitting rotation of said conduit about its longitudinal axis to vertically move each of said ends in opposite directions with respect to one another to permit leveling of said conduit.

7. The radiator hose hydrometer of claim 6 further comprising an offset adapter means secured to one of said ends respectively to permit rotation about the longitudinal axis of said conduit, thereby vertically moving said end to the opposing end thereof permitting leveling of said conduit.

8. In combination with a liquid cooled engine having an upper radiator hose extending therefrom to a radiator, a radiator hose hydrometer, comprising:

a substantially horizontally disposed transparent tubular conduit means interposed in said upper radiator hose and having first and second ends, said transparent tubular conduit permitting visual inspection of the color and level of the coolant passing through said radiator hose and said tubular conduit means, and means in said transparent tubular conduit means for indicating the specific gravity of the coolant passing therethrough and hence the approximate freezing point of the said coolant, means secured to at least one of said ends of said transparent tubular conduit for leveling said transparent tubular conduit, said means for leveling said conduit permitting determination of coolant level.

* * * * *